United States Patent [19]

Mendez-Nonell et al.

[11] Patent Number: 5,405,121
[45] Date of Patent: Apr. 11, 1995

[54] APPARATUS TO INDICATE THE OXYGEN CONTENT OF MOLTEN COPPER USING THE VIBRATION SIGNAL OF A GRAPHITE ROD IMMERSED INTO THE MOLTEN METAL

[75] Inventors: Manuel Mendez-Nonell, Ramos Arizpe; Juan Mendez-Nonell, Saltillo; Joel Chaparro-Gonzalez, Queretaro; Gregorio Vargas-Gutierrez, Saltillo, all of Mexico

[73] Assignee: Centro de Investigation y de Estudios Avanzados del IPN, Mexico

[21] Appl. No.: 235,274

[22] Filed: Apr. 29, 1994

[51] Int. Cl.⁶ .............................................. C21C 5/30
[52] U.S. Cl. ........................................ 266/99; 75/375; 75/386; 75/649
[58] Field of Search .................... 266/99; 75/649, 375, 75/386

[56] References Cited

U.S. PATENT DOCUMENTS

| | | | |
|---|---|---|---|
| 3,932,135 | 1/1976 | Di Stefano | 266/99 |
| 4,113,469 | 9/1978 | Grenfell | 75/649 |
| 4,135,915 | 1/1979 | Kennard | 75/386 |
| 4,149,877 | 4/1979 | Claes | 75/375 |
| 4,398,948 | 8/1983 | Emoto | 75/375 |
| 5,078,785 | 1/1992 | Ibaraki | 75/386 |

*Primary Examiner*—Peter D. Rosenberg
*Attorney, Agent, or Firm*—Laurence R. Brown

[57] ABSTRACT

The purpose of this invention is to present an apparatus consisting of a graphite rod, a vibration signal sensor, a signal processing unit, a data processing unit, and a data display unit to indicate the oxygen content of a copper melt. As such graphite rod is immersed into the molten metal it vibrates and the level of vibration is statistically correlated to the level of dissolved oxygen in the copper melt.

4 Claims, 2 Drawing Sheets

APPARATUS TO INDICATE THE OXYGEN CONTENT OF MOLTEN COPPER USING THE VIBRATION SIGNAL OF A GRAPHITE ROD IMMERSED INTO THE MOLTEN METAL

BACKGROUND OF THE INVENTION

It is well-established that, for the production of sound copper castings, complete elimination of hydrogen and oxygen is absolutely necessary. The method usually adopted in copper founding to avoid the steam reaction is the oxidation-reduction melting practice, which consists in keeping the hydrogen content of the melt low by increasing the oxygen content, which is subsequently removed by suitable deoxidation. For routine foundry control of gas induced porosity, a knowledge of the oxygen level in the melt prior to final deoxidation is required, since any excess of deoxidant is not only expensive but harmful. The method used in copper refineries, such as the solid electrolytic cell oxygen probe, are generally not suitable for small foundries due to the very high cost of consumables.

A simple, quick and inexpensive test for oxygen assessment in copper foundries relies on a carbon or graphite rod immersed in the oxidized copper melt. The rod will vibrate owing to the $C+[O] \rightarrow CO$ reaction occurring at its surface, the intensity of vibration being a function of the oxygen content. The test is reproducible and can readily determine the point at which the reaction becomes negligible, that is, when the oxygen is reduced to a low level.

J. L. Dion, A. Couture, and J. O. Edwards have used the graphite rod immersed test as a qualitative indication of the oxygen content in the liquid copper [1]. The authors reported only qualitative values of the vibration felt as moderate, slight and almost nil.

SUMMARY OF THE INVENTION

The object of the present invention is to provide an apparatus for measuring in a quantitative manner the oxygen content in liquid copper, using the vibration of an immersed graphite rod into the molten metal. This apparatus comprises a vibration sensor connected to a graphite rod, a signal processing unit where the electrical signal is processed, a data processing unit where such vibration signal is statistically correlated to the oxygen content of the molten copper, and a data display unit. A feature of this invention is the presentation of quantitative data to measure the oxygen content in liquid copper, compared to previous works that only provide qualitative and subjective manually sensed values.

DESCRIPTION OF THE PREFERRED EMBODIMENTS

Figure 1:
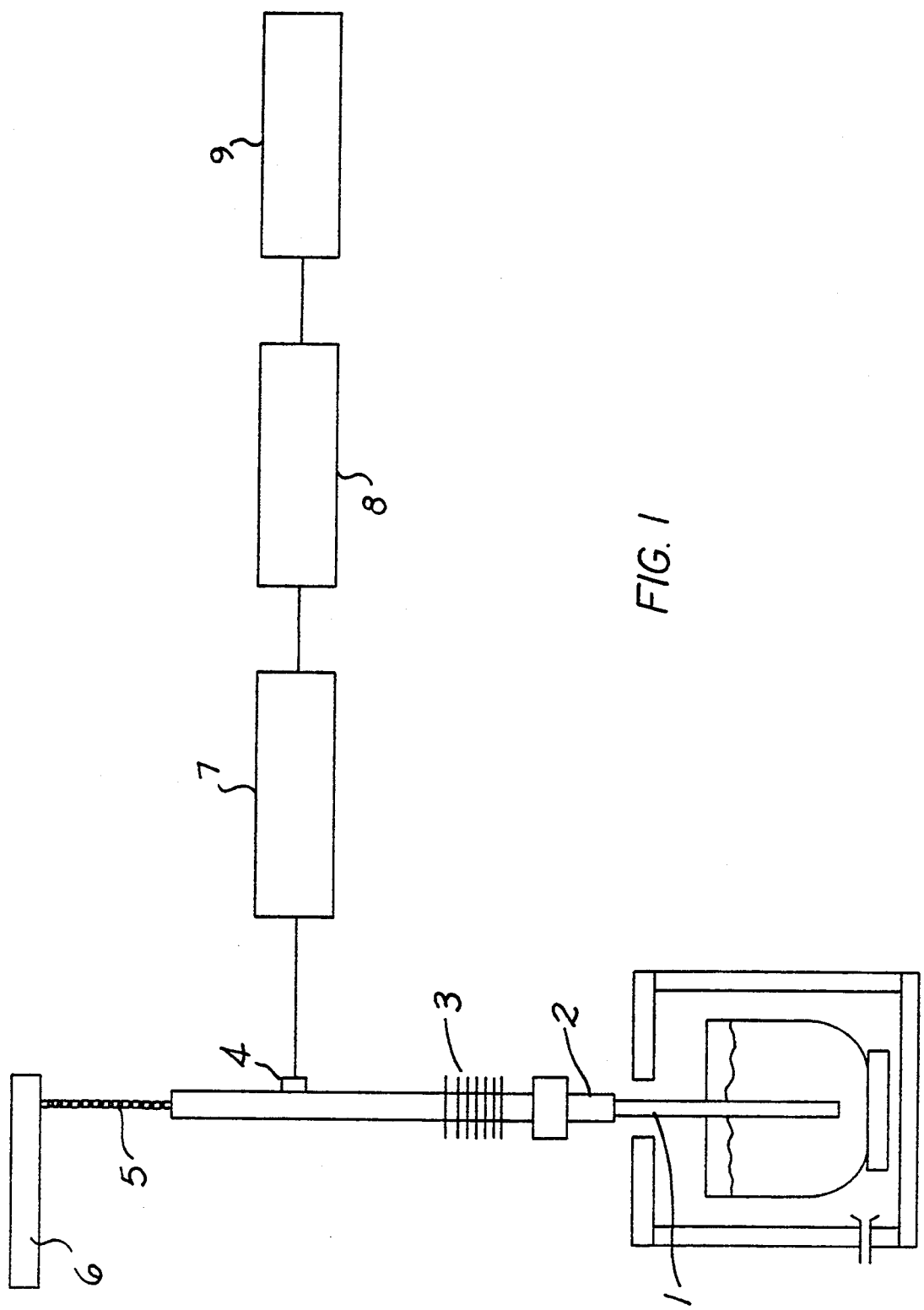

Referring to the drawing shown in FIG. 1, the apparatus of the present invention includes a graphite rod, generally designated 1, connected to a metallic support 2. In the preferred embodiments said metallic support has cooling vanes 3 to protect the vibration sensor 4, connected to said metallic support from heating. Said metallic support is itself supported by a chain 5 and a metallic frame 6.

In the preferred embodiment of this invention, it is desired to provide means for registering and converting the mechanical signal to an electrical signal. The conversion of such physical signal to an electrical signal is carried out by the sensor 4 from which it is transmitted to a signal processing unit 7. Although it is not mandatory, the amplified electrical signal is transmitted to a data processing unit 8 where such electrical signal is statistically correlated to the oxygen content. Finally, the oxygen content is displayed through a display data unit 9.

Figure 2:
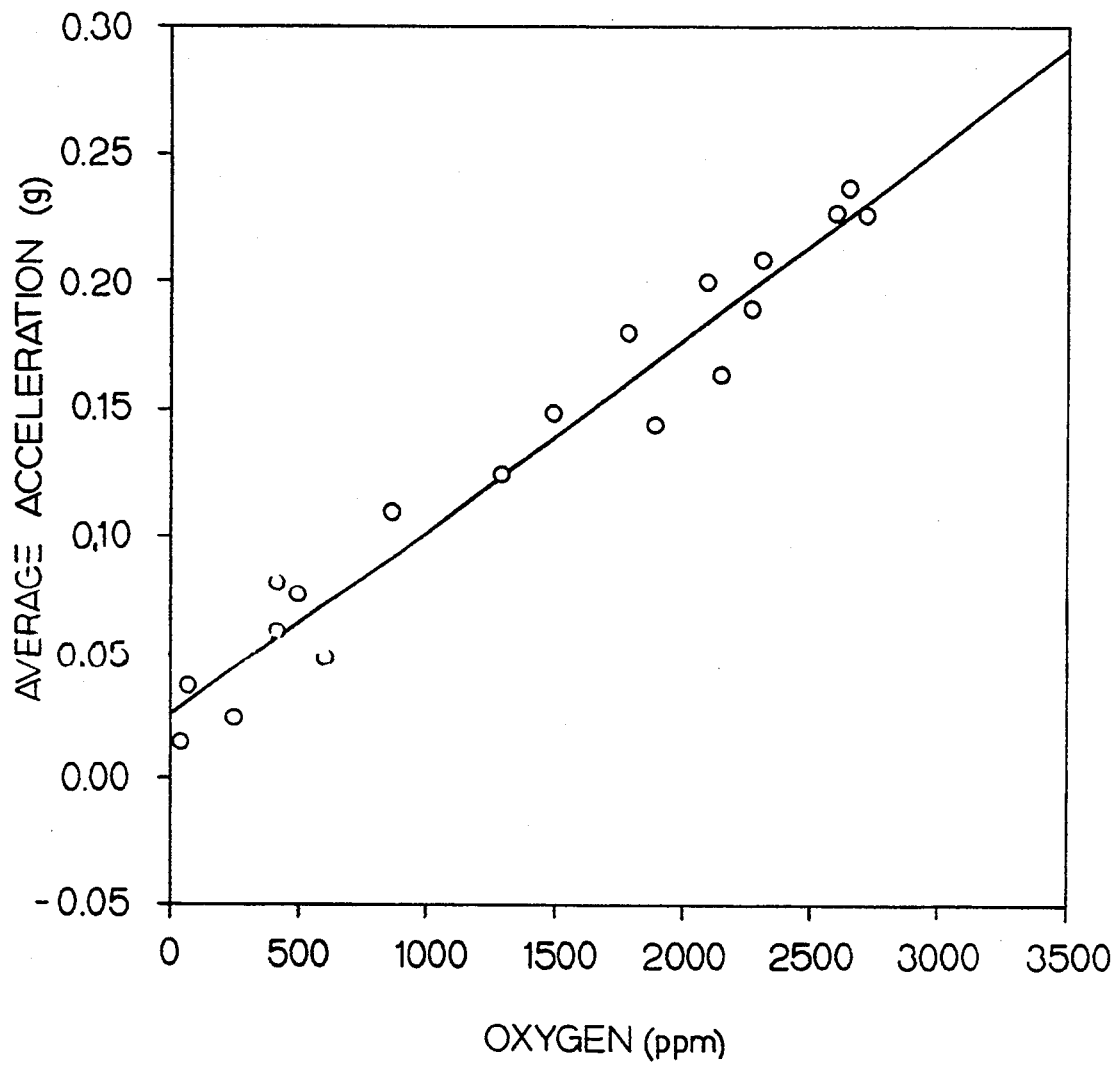

The vibration of the graphite rod may be characterized by its movement, frequency, speed and acceleration. However, our previous experiences show that the measurement of the vibrations acceleration may be adequately correlated to the level of dissolved oxygen in the liquid metal. The dissolved oxygen content measurements were carried out continuously in a series of trials using an electrochemical cell. This information was simultaneously measured and statistically correlated to the average acceleration. FIG. 2 shows the effect of copper deoxidation on the average acceleration of the graphite rod. The graphic shows a decrease of the vibration acceleration as the content of dissolved oxygen is reduced.

The vibration technique proved to be sensitive to slight changes in the oxidation state of the copper baths. This technique detected changes corresponding to different operation conditions such as melting units, protective atmospheres, and level of deoxidant additions.

What we claim is:

1. Apparatus to indicate quantitatively oxygen content of molten copper using a vibration signal of a graphite rod immersed into molten copper, said apparatus comprising the following components: a graphite rod for immersion in said molten copper, means for connecting said rod to a metallic support, said metallic support mechanically suspending said rod for vibration in the molten copper, a vibration sensor located on said metallic support that converts mechanical vibration of said rod to a proportional electrical signal, said vibration sensor being electrically connected to a signal processing unit which processes said electrical signal, a data processing unit coupled to receive the electrical signal for statistically correlating the signal to indicate quantitatively the dissolved oxygen content in the molten copper as a function of vibration of the graphite rod and a display data unit coupled to said data processing unit for displaying the oxygen content in said molten copper.

2. The apparatus of claim 1 wherein the graphite rod is suspended to vibrate responsive to a carbon and oxygen reduction reaction occurring at the surface of said graphite rod.

3. The apparatus of claim 1 wherein the data processing unit converts average acceleration of the rod to a quantity of dissolved oxygen content in the molten copper.

4. The apparatus of claim 3 operable over a range of oxygen in the molten copper less than 2500 parts per million.

* * * * *